United States Patent
Yang et al.

(10) Patent No.: US 10,266,541 B2
(45) Date of Patent: Apr. 23, 2019

(54) JOINT PRODUCTION METHOD AND DEVICE FOR AZIRIDINE, PIPERAZINE AND TRIETHYLENEDIAMINE

(71) Applicant: XI'AN MODERN CHEMISTRY RESEARCH INSTITUTE, Shaanxi (CN)

(72) Inventors: Jianming Yang, Shaanxi (CN); Suning Mei, Shaanxi (CN); Qinwei Yu, Shaanxi (CN); Feng Hui, Shaanxi (CN); Jun Yuan, Shaanxi (CN); Wei Wang, Shaanxi (CN); Yani Li, Shaanxi (CN); Weiqiang Wang, Shaanxi (CN); Jian Lu, Shaanxi (CN)

(73) Assignee: XI'AN MODERN CHEMISTRY RESEARCH INSTITUTE, Shaanxi (CN)

( * ) Notice: Subject to any disclaimer, the term of this patent is extended or adjusted under 35 U.S.C. 154(b) by 0 days.

(21) Appl. No.: 15/817,045

(22) Filed: Nov. 17, 2017

(65) Prior Publication Data

US 2018/0093993 A1    Apr. 5, 2018

Related U.S. Application Data

(62) Division of application No. 15/105,883, filed as application No. PCT/CN2014/086019 on Sep. 5, 2014, now Pat. No. 9,850,250.

(30) Foreign Application Priority Data

Dec. 18, 2013   (CN) .......................... 2013 1 0698872

(51) Int. Cl.
| | | |
|---|---|---|
| *C07D 487/08* | (2006.01) | |
| *B01J 27/18* | (2006.01) | |
| *C07D 203/02* | (2006.01) | |
| *C07D 295/023* | (2006.01) | |
| *B01J 21/02* | (2006.01) | |
| *B01J 21/06* | (2006.01) | |
| *B01J 19/00* | (2006.01) | |
| *B01J 31/02* | (2006.01) | |

(52) U.S. Cl.
CPC ........ *C07D 487/08* (2013.01); *B01J 19/0046* (2013.01); *B01J 21/02* (2013.01); *B01J 21/063* (2013.01); *B01J 27/18* (2013.01); *B01J 31/0237* (2013.01); *C07D 203/02* (2013.01); *C07D 295/023* (2013.01); *B01J 2219/0072* (2013.01); *B01J 2219/00452* (2013.01); *B01J 2219/00495* (2013.01); *B01J 2219/00585* (2013.01); *B01J 2231/44* (2013.01); *B01J 2531/002* (2013.01)

(58) Field of Classification Search
CPC ...... B01J 19/0046; B01J 21/02; B01J 21/063; B01J 27/18; B01J 31/0237; C07D 487/08; C07D 295/023; C07D 203/02
USPC ......................................................... 544/352
See application file for complete search history.

(56) References Cited

U.S. PATENT DOCUMENTS

| 4,337,175 A | 6/1982 | Ramirez |
| 4,774,218 A | 9/1988 | Shimasaki et al. |

FOREIGN PATENT DOCUMENTS

| CN | 86 1 08963 A | 8/1987 |
| CN | 1182744 A | 5/1998 |
| CN | 101284244 A | 10/2008 |
| CN | 102000602 A | 4/2011 |
| CN | 103657694 A | 3/2014 |
| CN | 103819381 A | 5/2014 |
| EP | 0 227 461 A2 | 7/1987 |
| JP | 63-23744 A | 2/1988 |
| JP | 2012-192337 A | 10/2012 |

OTHER PUBLICATIONS

International Search Report, dated Dec. 17, 2014, for International Application No. PCT/CN2014/086019, 6 pages.

*Primary Examiner* — Kahsay Habte
(74) *Attorney, Agent, or Firm* — Seed Intellectual Property Law Group LLP

(57) ABSTRACT

Disclosed are a joint production method and device for aziridine, piperazine and triethylenediamine. The method comprises: reaction 1, preparing piperazine and triethylenediamine by taking ethanol amine as a raw material under the existence of a cyclamine catalyst; reaction 2, preparing aziridine by taking the ethanol amine as the raw material under the existence of a catalyst B; and taking heat released in the reaction 1 as a heat source of heat absorption in the reaction 2. The device comprises a reactor 1 for carrying out the reaction 1 and the heat exchange between reaction materials of the reaction 1 and the raw material of the reaction 2 and a reactor 2 for carrying out the reaction 2. According to the present invention, the same raw material, namely the ethanol amine is adopted, aziridine, piperazine and triethylenediamine can be produced in a joint manner, the heat released in the reaction 1 is used for preheating materials in the reaction 2, so that heat coupling between the reactions is implemented, energy conservation is facilitated and competitiveness of the device is improved.

4 Claims, 1 Drawing Sheet

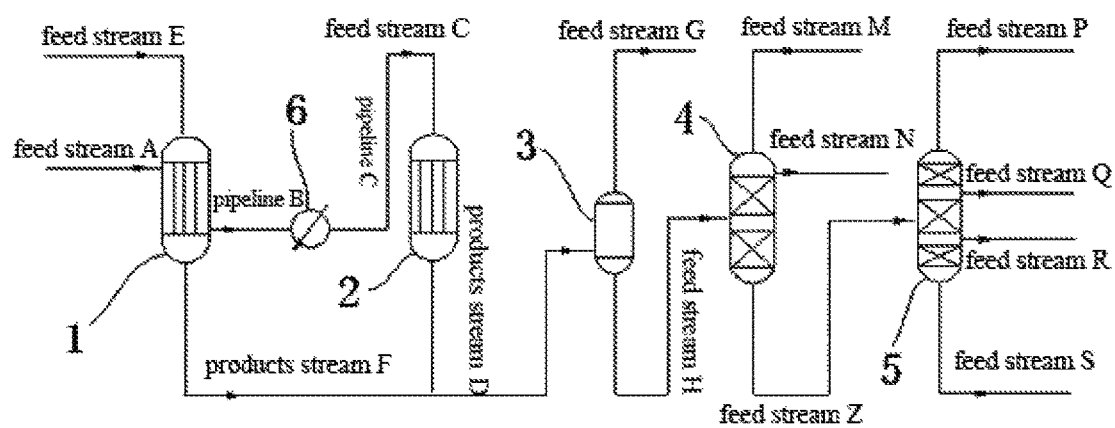

JOINT PRODUCTION METHOD AND DEVICE FOR AZIRIDINE, PIPERAZINE AND TRIETHYLENEDIAMINE

TECHNICAL FIELD

The present invention belongs to the field of chemical technology, and particularly relates to a joint production method for aziridine, piperazine and triethylenediamine.

BACKGROUND

Aziridine, also referred to as ethyleneimine, has found a wide application in the fields of medicine, pesticide, high-energy fuel, bonding agent, photographic material, cross-linking agent, and the like. Piperazine is an important pharmaceutical intermediate and a fine chemicals raw material. Triethylenediamine is one of the most important polyurethane catalysts.

A preparation method for ethylenimine by using the complex oxide of a niobium oxide or a tantalum oxide and an alkaline earth oxide (BaO) as a catalyst is disclosed in U.S. Pat. No. 4,337,175. By using monoethanolamine (MEA) as the raw material, the preparation method was carried out in the presence of $NH_3$ as inert protective atmosphere at the temperature of 390° C. to 400° C., and as a consequence, the MEA conversion was 13.87% with selectivity to ethylenimine of 82.09%. Further, a small amount of acetaldehyde, ethylene amine, pyrazine and alkylpyrazine were also generated.

A silicon-containing catalyst with an elemental composition of Sia/Xx/Yy/Ob is disclosed in EP0227461, wherein X is any element selected from alkaline metals or alkaline earth metals; Y is at least one element selected from the group consisting of B, Al, Ti, Zr, Sn, Zn, and Ce; the suffixes a, b, x, and y represent the atomic ratios of the elements Si, X, Y and O respectively, and when a=1, x=0.05~1 and y=0~0.1, and b is a value determined by a, x and y. By using monoethanolamine as the raw material, an inert gas (such as $NH_3$, $N_2$ or $H_2$) as a diluent, and the ratio of ethanol amine to the inert gas being 2~50%, the reaction was generally carried out under atmospheric pressure at the temperature of 300° C. to 500° C., with the optimum space velocity of the reactant gas of 500 to 3,000 $h^{-1}$. As a consequence, the optimum conversion (mol) of ethanolamine was 56.5%, the selectivity (mol) to aziridine was 89.1%.

In the prior arts, the raw materials such as monoethanolamine, diethanolamine, ethylenediamine, aminoethyl piperazine, and hydroxyethyl piperazine are generally used in the production of piperazine and triethylenediamine.

A production of triethylenediamine using surface acidity deactivated zeolite catalysts is disclosed in CN97123116.8. By using monoethanolamine and piperazine as reaction materials, the reaction was carried out at 350° C., with the liquid hourly space velocity of 0.52 $h^{-1}$. As a consequence, the conversion (mol) was 72%, and the selectivity (mol) to TEDA was 30%.

New approaches for aziridine, piperazine and/or triethylenediamine are provided in the abovementioned documents. The reactions are acid catalyzed reactions, and solid acid catalysts may be used. However, the catalysts used in the above methods differ greatly, so that aziridine, piperazine and/or triethylenediamine cannot be produced jointly and simultaneously in a same device.

No reference document, in which a joint production method for aziridine, piperazine and triethylenediamine by using ethanolamine as a raw material is disclosed, is searched.

DISCLOSURE OF THE INVENTION

With respect to the defects or deficiencies in the prior art, one objective of the present invention is to provide a joint production method for aziridine, piperazine and triethylenediamine, so as to efficiently save energy, jointly produce aziridine, piperazine and triethylenediamine at the same time, and improve competitiveness of the device.

To this end, the present invention provides a joint production method for aziridine, piperazine and triethylenediamine, comprising:

reaction 1, preparing piperazine and triethylenediamine by taking ethanol amine as a raw material in the presence of a cyclamine catalyst; and reaction 2, preparing aziridine by taking the ethanol amine as a raw material in the presence of a catalyst B;

wherein the catalyst B is $Ti_aP_bB_cX_dY_eO_f$, wherein X is an alkali earth metal, Y is an alkali metal, O is an oxygen element; a, b, c, d, e, and f are the mole ratios of each element atom, and a=1, b=0.02~0.2, c=0.002~0.02, d=0.01~0.1, e=0.001~0.01, and f is dependent on a, b, c, d, and e; and the heat released in the reaction 1 is used as a heat source for the reaction 2.

Preferably, the temperature adopted in the reaction 1 is in a range of 300° C. to 400° C.

Preferably, the temperature adopted in the reaction 2 is in a range of 350° C. to 450° C.

Preferably, the preparation method for the catalyst B comprises:
mixing a compound comprising X, a compound comprising Y, a metatitanic acid, a phosphate, and a boronic acid; adding graphite thereto, then compressing the resulting mixture and shaping; and calcining the shaped mixture in the presence of oxygen at a temperature of 300° C. to 400° C. followed by further calcining at a temperature of 600° C. to 900° C., thereby obtaining the catalyst B;

wherein the compound comprising X is an oxide, a hydroxide, a halide, a nitrate, a carbonate, or a sulfate of X;

the compound comprising Y is an oxide, a hydroxide, a halide, a nitrate, a carbonate, or a sulfate of Y;

the phosphate is ammonium phosphate, diammonium phosphate, or ammonium dihydrogen phosphate;

the graphite is used in a mount of 1%~4% by mass of the mixture of the compound comprising X, the compound comprising Y, the metatitanic acid, the phosphate, and the boronic acid.

Further, the joint production method for aziridine, piperazine and triethylenediamine comprises a process of separating products comprising:

mixing the reaction products obtained in the reaction 1 and the reaction 2; flashing the mixture stream to separate nitrogen, which is an inert gas, distilling the remaining mixture stream to remove ammonia, obtaining aziridine through separation; then rectifying the resultant mixture stream to obtain piperazine and triethylenediamine through separation.

With respect to the defects or deficiencies in the prior art, another objective of the present invention is to provide a joint production device for aziridine, piperazine and triethylenediamine.

To this end, the present invention provides a joint production device for aziridine, piperazine and triethylenediamine, comprising:

a reactor 1, for carrying out the reaction 1 and the heat exchange between the reaction materials of the reaction 1 and the raw materials of the reaction 2;

a reactor 2, for carrying out the reaction 2; and a combination separation unit, comprising a flash unit, an aziridine separation unit, and a polyamine separation unit connected successively, wherein the flash unit is used for separating nitrogen, which is an inert gas, the aziridine separation unit is used for separating aziridine, and the polyamine separation unit is used for separating piperazine and triethylenediamine.

Preferably, the flash unit is a flash tower, wherein the flash tower has a theoretical plate number of 1 to 3, a temperature in a range of 0° C. to 30° C., and a pressure in a range of 0.5 MPa to 2.5 MPa.

Preferably, the aziridine separation unit is a rectifying tower filled with structured packing, wherein the rectifying tower has a theoretical plate number of 30 to 50, a top temperature in a range of 20° C. to 50° C., a bottom temperature in a range of 150° C. to 280° C., a pressure in a range of 0.5 MPa to 2.5 MPa; feeding location is at the 15$^{th}$ to 25$^{th}$ theoretical plates; ammonia in a gas phase and remaining nitrogen are collected from the top of the rectifying tower, an aziridine product stream is collected in a liquid phase from a side-draw and the side-draw collection position is located at the 2$^{th}$ to 8$^{th}$ theoretical plates.

Preferably, the polyamine separation unit is a rectifying tower filled with structured packing, wherein the rectifying tower has a theoretical plate number of 40 to 70, a top temperature in a range of 60° C. to 110° C., a bottom temperature in a range of 150° C. to 180° C., a pressure in a range of 30 kPa to 100 kPa; feeding location is at the 20$^{th}$ to 30$^{th}$ theoretical plates; ethanediamine and water are collected from the top of the rectifying tower, a piperazine product stream is collected in a gas phase from a side-draw at the 20$^{th}$ to 40$^{th}$ theoretical plates, a mixture of triethylenediamine and ethanol amine is collected from a side-draw at the 38$^{th}$ to 58$^{th}$ theoretical plates, and the remaining ethanol amine, aminoethyl piperazine, and hydroxyethyl piperazine are collected from the bottom of the rectifying tower.

The advantages of the present invention relative to the prior art may lie in that:

In the present invention, aziridine, piperazine and triethylenediamine may be produced jointly from a same raw material ethanol amine. The heat released in the reaction 1 is used for preheating the materials of the reaction 2, so that the heat coupling between the above reactions is achieved, energy conservation is facilitated and competitiveness of the device is improved.

At the same time, the present invention may be used in the heat coupling production process of aziridine, piperazine and triethylenediamine from various amino alcohols as raw materials.

DESCRIPTION OF THE DRAWINGS

FIG. 1 is a schematic flow chart of the production process of aziridine, piperazine and triethylenediamine.

SPECIFIC MODE FOR CARRYING OUT THE PRESENT INVENTION

Reaction 1 is carried out at the reaction temperature of 300° C. to 400° C. by taking ethanol amine as a raw material in the presence of the cyclamine catalyst, so that piperazine and/or triethylenediamine may be produced with high selectivity. The reaction (1) is an exothermic reaction:

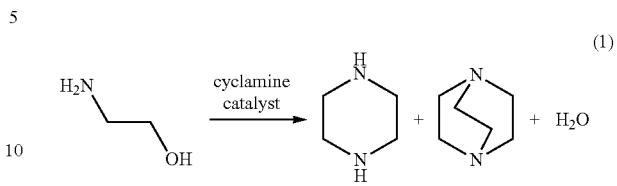

The ethanol amine as a raw material is reacted at the reaction temperature of 350° C. to 450° C. in the presence of the catalyst B, so that aziridine may be produced with high selectivity. The reaction (2) is an endothermic reaction:

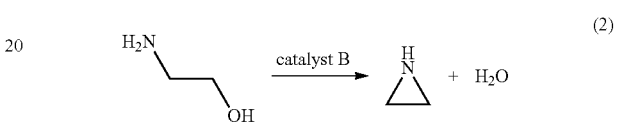

The heat coupling between the above reactions may be achieved by using ethanol amine as a raw material. At the same time, aziridine, piperazine and triethylenediamine may be produced jointly from the same raw material, thereby improving the competitiveness of the device.

According to the present invention, monoethanolamine is used as a raw material. Isopropanolamine, 2-methylaminopropanol, and other amino alcohol compounds may also be used.

The cyclamine catalyst according to the present invention is the catalyst as described in CN102000602A.

In the catalyst B according to the present invention, preferably, X is magnesium, Y is cesium, b=0.2, c=0.01, d=0.1, e=0.01, f=2.62, or X is barium, Y is potassium, b=0.05, c=0.02, d=0.1, e=0.01, f=2.27.

The structured packing according to the present invention is stainless steel wire mesh or plate wave packing.

The reaction process performed in the device according to the present invention is illustrated as follows:

As described in FIG. 1, a preheated feed stream E mainly composed of ethanol amine, water, and nitrogen or ammonia as an inert gas are introduced into a reactor 1 with tube pass and shell pass structure, the tube pass of which is filled with a cyclamine catalyst; the contact reaction of the feed stream E, which is an exothermic reaction, is carried out in the presence of the cyclamine catalyst, and the heat released is conducted to and thereby preheats the materials of the shell pass through the tube wall of the tube pass of the reactor 1; the obtained products stream F comprising the inert gas, water, ammonia, unreacted ethanol amine and products, i.e., piperazine, triethylenediamine and a small amount of ethylenediamine, hydroxyethyl piperazine, and aminoethyl piperazine is discharged from the bottom of the reactor 1 and introduced into the combination separation unit.

A preheated feed stream A mainly composed of ethanol amine, and nitrogen as an inert gas are introduced into the shell pass of the reactor 1, and preheated by the heat conducted through the tube pass of the reactor 1; the preheated mixture is discharged from the shell pass, introduced into an intermediate heat exchanger 6 through a pipeline B, and further heated to a certain temperature, then introduced into a reactor 2 with tube pass and shell pass structure through a pipeline C, wherein the tube pass of the reactor 2 is filled with a catalyst B; the contact reaction of a feed stream C is carried out in the presence of the catalyst B, and the obtained products stream D comprising the inert gas nitrogen, water, unreacted ethanol amine, and products i.e., aziridine, and the light component ethylene amine is discharged from the bottom of the reactor 2 and introduced into the combination separation unit.

The reaction products stream introduced into the combination separation unit comprises the inert gas nitrogen, ammonia, water, aziridine, unreacted ethanol amine, products i.e., piperazine, triethylenediamine, ethylenediamine, aminoethyl piperazine, and hydroxyethyl piperazine. The reaction products stream is separated in a combination separation unit which comprises a flash unit 3, an aziridine separation unit 4, and a polyamine separation unit 5. The aziridine product stream is collected in a liquid phase from a side-draw of the aziridine separation unit 4, and piperazine and triethylenediamine are collected in a gas phase from a side-draw of the polyamine separation unit 5.

The present invention will be further explained and described below with reference to the following preferable examples provided by the inventor, but is not limited thereto.

EXAMPLE 1

Referring to FIG. 1, the process of the reaction (1): a feed stream E with a flow rate 2876.34 kg/h was preheated to 330° C., introduced to the tube pass of the reactor 1 in which a cyclamine catalyst was filled; the contact reaction of the feed stream E was carried out in the presence of the cyclamine catalyst under a reaction pressure of 1.0 MPa with a heat release power of 118 kW; and the obtained products stream F was discharged from the bottom of the reactor 1 and introduced into a separation unit.

The composition of the feed stream E by mass percentage was:

$NH_3$: 15.1%, MEA: 71.3%, and $H_2O$: 13.5%.

The composition of the products stream F by mass percentage was:

$NH_3$: 15.0%, MEA: 24.0%, EDA: 5.0%, $H_2O$: 27.0%, PIP: 14.7%, AEP: 2.6%, TEDA: 10.3%, HEP: 0.9%, and noncondensable gas: 0.3%.

The process of the reaction (2): a feed stream A with a flow rate 13853.48 kg/h was preheated to 290° C., introduced to the shell pass of the reactor 1, heated to a temperature of 314° C. through the heat conducted by the tube pass of the reactor 1, discharged from the shell pass, then introduced into an intermediate heat changer 6 through a pipeline B and further heated to a temperature of 380° C. with an heating power of 329 kW, and introduced into a reactor 2 filled with a catalyst B through a pipeline C, to carry out the contact reaction under a reaction pressure of 0.1 MPa; the obtained products stream D was discharged from the bottom of the reactor 2 and introduced into a separation unit.

The composition of the feed stream C by mass percentage was:

$N_2$: 17.9% and MEA: 82.1%.

The composition of the products stream D by mass percentage was:

$N_2$: 82.1%, $H_2O$: 2.37%, aziridine: 4.67%, MEA: 9.84%, ethylene amine: 0.35%, piperazine and derives thereof: 0.41%, and others: 0.3%.

The heat released from the process of the reaction (1) was used as the heat required for the process of the reaction (2), so that approximately 26.4% of energy was saved.

In this Example 1, the flash unit 3 was a flash tower, wherein the flash tower had a theoretical plate number of 2, a temperature of 20° C., and a pressure of 2.0 MPa.

The composition of the feed stream G by mass percentage was:

$N_2$: 99.5% and others: 0.5%.

The composition of the feed stream H by mass percentage was:

$N_2$: 4.1%, $H_2O$: 9.3%, aziridine: 21.0%, ethanol amine: 38.7%, piperazine: 12.0%, triethylenediamine: 8.3%, ethylenediamine: 4.1%, aminoethyl piperazine and hydroxyethyl piperazine: 2.2%, and ethylene amine: 0.35%.

The aziridine separation unit 4 was a rectifying tower filled with structured packing, wherein the rectifying tower had a theoretical plate number of 45, a top temperature of 23.3° C., a bottom temperature of 226° C., and a pressure of 2.0 MPa. The feeding location was at the $18^{th}$ theoretical plate. Ammonia in a gas phase and remaining nitrogen were collected from the top of the rectifying tower, and an aziridine product stream was collected in a liquid phase from a side-draw, the collection position from the side-draw was located at the $3^{th}$ theoretical plate.

The composition of the feed stream M by mass percentage was:

$N_2$: 93.2%, $NH_3$: 5.4%, and aziridine: 1.3%.

The composition of the feed stream N by mass percentage was:

Aziridine: 99.8%, and others: 0.2%.

The composition of the feed stream Z by mass percentage was:

$H_2O$: 12.5%, ethanol amine: 51.8%, piperazine: 16.0%, triethylenediamine: 11.1%, ethylenediamine: 5.49%, and aminoethyl piperazine and hydroxyethyl piperazine: 3.0%.

The polyamine separation unit 5 was a rectifying tower filled with structured packing, wherein the rectifying tower had a theoretical plate number of 60, a top temperature of 86.3° C., a bottom temperature of 149.4° C., and a pressure of 50 kPa. The feeding location was at the $40^{th}$ theoretical plate. A feed stream 12 comprising ethanediamine and water was collected from the top of the rectifying tower; a piperazine product stream was collected in a gas phase from a side-draw at the $30^{th}$ theoretical plate; a mixture of triethylenediamine and ethanol amine was collected from a side-draw at the $48^{th}$ theoretical plate; and the remaining ethanol amine, aminoethyl piperazine, and hydroxyethyl piperazine were collected from the bottom of the rectifying tower.

The composition of the feed stream P by mass percentage was:

Ethanediamine: 30.3% and $H_2O$: 69.5%.

The composition of the feed stream Q by mass percentage was:

Piperazine: 99.1% and others: 0.9%.

The composition of the feed stream R by mass percentage was:

Triethylenediamine: 56.7%, ethanol amine: 43.2%, and others: 0.1%.

The composition of the feed stream S by mass percentage was:

Ethanol amine: 93.4%, aminoethyl piperazine and hydroxyethyl piperazine: 5.3%, and others: 1.3%.

EXAMPLE 2

Referring to FIG. 1, the process of the reaction (1): a feed stream E with a flow rate 4,183.02 kg/h was preheated to 330° C., introduced to the tube pass of the reactor 1 in which a cyclamine catalyst was filled; the contact reaction of the feed stream E was carried out in the presence of the cyclamine catalyst under a reaction pressure of 1.0 MPa with a heat release power of 173.3 kW; and the obtained products stream F was discharged from the bottom of the reactor 1 and introduced into the combination separation unit.

The composition of the feed stream E by mass percentage was:

$NH_3$: 14.3%, MEA: 72.0% and $H_2O$: 13.7%.

The composition of the products stream F by mass percentage was:

$NH_3$: 14.5%, MEA: 24.2%, EDA: 4.3%, $H_2O$: 26.4%, PIP: 15.4%, AEP: 1.6%, TEDA: 13.3%, HEP: 0%, and noncondensable gas: 0.3%.

The process of the reaction (2): a feed stream A with a flow rate 20,333.3 kg/h was preheated to 290° C., introduced to the shell pass of the reactor 1, heated to a temperature of 314° C. through the heat conducted by the tube pass of the reactor 1, discharged from the shell pass, then introduced into an intermediate heat changer 6 through a pipeline B and further heated to a temperature of 400° C. with an heating power of 618.3 kW, and introduced into a reactor 2 filled with a catalyst B through a pipeline C to carry out a contact reaction under a reaction pressure of 0.1 MPa; and the obtained products stream D was discharged from the bottom of the reactor 2 and introduced into the combination separation unit.

The composition of the feed stream C by mass percentage was:

$N_2$: 17.9% and MEA: 82.1%.

The composition of the products stream D by mass percentage was:

$N_2$: 81.6%, $H_2O$: 2.58%, aziridine: 4.62%, MEA: 8.32%, ethylene amine: 0.55%, piperazine and derives thereof: 0.82%, and others: 1.51%.

The heat released from the process of the reaction (1) was used as the heat required for the process of the reaction (2), so that approximately 21.9% of energy was saved.

EXAMPLE 3

Referring to FIG. 1, the process of this Example 3 was substantially the same as that of Example 1 except that the feed stream E was preheated to a temperature of 360° C.; the feed stream A was preheated to a temperature of 300° C., introduced into the shell pass of the reactor 1, and heated to a temperature of 329° C. by the heat conducted through the tube pass of the reactor 1.

The heat released from the process of the reaction 1 was 224.3 kW, and the heating power of the intermediate heat exchanger 6 was 348.3 kW.

The heat released from the process of the reaction (1) was used as the heat required for the process of the reaction (2), so that approximately 39.1% of energy was saved.

EXAMPLE 4

Referring to FIG. 1, the process of this Example 4 was essentially the same as that of Example 1 except that the feed stream E was preheated to a temperature of 340° C.; the feed stream A was preheated to a temperature of 280° C., introduced into the shell pass of the reactor 1, heated to a temperature of 321° C. by the heat conducted through the tube pass of the reactor 1, discharged from the shell pass, introduced into the intermediate heat exchanger 6 with a heating power of 468.2 kW through a pipeline B and further heated to a temperature of 400° C.

The heat released from the process of the reaction 1 was 198.9 kW.

The heat released from the process of the reaction (1) was used as the heat required for the process of the reaction (2), so that approximately 29.8% of energy was saved.

What is claimed is:

1. A device for production of aziridine, piperazine and triethylenediamine, the device comprising:
   a first reactor, for carrying out a first reaction and for heat exchange between reaction materials of the first reaction and raw materials of a second reaction;
   a second reactor, for carrying out the second reaction; and
   a combination separation unit, comprising a flash unit, an aziridine separation unit, and a polyamine separation unit connected successively, wherein the flash unit is configured for separating nitrogen, the aziridine separation unit is configured for separating aziridine, and the polyamine separation unit is configured for separating piperazine and triethylenediamine,
   wherein:
      the first reaction comprises preparing piperazine and triethylenediamine by taking ethanol amine as a raw material in the presence of a cyclamine catalyst;
      the second reaction comprises preparing aziridine by taking ethanol amine as a raw material in the presence of a catalyst B; and
      the catalyst B is $Ti_aP_bB_cX_dY_eO_f$, wherein: X is an alkaline earth metal, Y is an alkaline metal, O is an oxygen element; a, b, c, d, e, and f are the mole ratios of each element atom, and a=1, b=0.02~0.2, c=0.002~0.02, d=0.01~0.1, e=0.001~0.01, and f is dependent on a, b, c, d, and e.

2. The device of claim 1, wherein the flash unit is a flash tower having a theoretical plate number of 1 to 3, and is configured for operation at a temperature in a range of 0° C. to 30° C., and a pressure in a range of 0.5 MPa to 2.5 MPa.

3. The device of claim 1, wherein the aziridine separation unit is configured for operation at a top temperature in a range of 20° C. to 50° C., a bottom temperature in a range of 150° C. to 280° C., and a pressure in a range of 0.5 MPa to 2.5MPa and comprises:
   a) a rectifying tower filled with structured packing and having a theoretical plate number of 30 to 50;
   b) a feeding location at the $15^{th}$ to $25^{th}$ theoretical plates;
   c) a gas-phase ammonia nitrogen collection area at the top of the rectifying tower; and
   d) a side draw located in a position between the $2^{nd}$ to $8^{th}$ theoretical plates for collecting a liquid aziridine product stream.

4. The device of claim 1, wherein the polyamine separation unit is configured for operation at a top temperature in a range of 60° C. to 110° C., a bottom temperature in a range of 150° C. to 180° C., and a pressure in a range of 30 kPa to 100 kPa and comprises:
   a) a rectifying tower filled with structured packing and having a theoretical plate number of 40 to 70;
   b) a feeding location in a position between the $20^{th}$ to $30^{th}$ theoretical plates;
   c) an ethanediamine and water collection area at the top of the rectifying tower;
   d) a side draw located at a position between the $20^{th}$ and $40^{th}$ theoretical plates for collecting a gas-phase piperazine product stream;
   e) a side draw located at a position between the $38^{th}$ to $58^{th}$ theoretical plates for collecting a mixture of triethylenediamine and ethanol amine; and f) a collection area for collecting ethanol amine, aminoethyl piperazine, and hydroxyethyl piperazine at the bottom of the rectifying tower.

\* \* \* \* \*